US010791931B2

(12) United States Patent
Fisher et al.

(10) Patent No.: US 10,791,931 B2
(45) Date of Patent: Oct. 6, 2020

(54) IMAGING REDUCTIONS IN CEREBROVASCULAR REACTIVITY

(71) Applicant: THORNHILL SCIENTIFIC INC., Toronto (CA)

(72) Inventors: Joseph A. Fisher, Toronto (CA); Olivia Sobczyk, Toronto (CA); Adrian P. Crawley, Toronto (CA); Julien Poublanc, Toronto (CA); Kevin Sam, Toronto (CA); Daniel M. Mandell, Toronto (CA); David J. Mikulis, Toronto (CA); James Duffin, Toronto (CA)

(73) Assignee: THORNHILL SCIENTIFIC INC., North York (CA)

( * ) Notice: Subject to any disclaimer, the term of this patent is extended or adjusted under 35 U.S.C. 154(b) by 1006 days.

(21) Appl. No.: 14/859,809

(22) Filed: Sep. 21, 2015

(65) Prior Publication Data
US 2016/0220115 A1 Aug. 4, 2016

Related U.S. Application Data

(63) Continuation of application No. 14/614,310, filed on Feb. 4, 2015, now abandoned.

(51) Int. Cl.
*A61B 5/026* (2006.01)
*A61B 5/00* (2006.01)
(Continued)

(52) U.S. Cl.
CPC .......... *A61B 5/0042* (2013.01); *A61B 5/0036* (2018.08); *A61B 5/0263* (2013.01);
(Continued)

(58) Field of Classification Search
CPC ............ A61B 2576/026; A61B 5/0042; A61B 5/0205; A61B 5/0263; A61B 5/14542;
(Continued)

(56) References Cited

U.S. PATENT DOCUMENTS

| 2007/0225606 A1 | 9/2007 | Naghavi et al. |
| 2008/0275340 A1 | 11/2008 | Beach et al. |
| 2013/0010927 A1 | 1/2013 | Seppi et al. |

FOREIGN PATENT DOCUMENTS

| CA | 2419622 | 9/2003 |
| WO | WO02/01242 | 1/2002 |

(Continued)

OTHER PUBLICATIONS

International Search Report on corresponding PCT application (PCT/CA2015/000274) from International Searching Authority (CIPO) dated Jul. 17, 2015.
(Continued)

*Primary Examiner* — Jonathan Cwern
(74) *Attorney, Agent, or Firm* — Perry + Currier Inc.

(57) ABSTRACT

A system for detecting an abnormality in a subject's cerebrovascular response to a vasoactive stimulus in at least one region of interest (ROI) of the subject's brain The system comprises a system for generating the vasoactive stimulus (SVS), the SVS including a gas delivery device and a control system operable to deliver controlled amounts of carbon dioxide effective to attain at least one of a series of targeted increments or decrements in the subject's $PetCO_2$, for a series of respective intervals; an imaging system comprising an MRI scanner for generating response signals corresponding to the subject's vasoactive response to the vasoactive stimulus; and a computer for analyzing the response signals, the computer including program code for computing at least one value representing a quantitative measure of the subject's cerebrovascular reactivity for the ROI, wherein the at
(Continued)

least one value is obtained for a specific portion of the subject's vasoactive response in the ROI, the specific portion of the subject's vasoactive response corresponding to a sub-series of the at least one of a series of targeted increments or decrements in the subject's PetCO$_2$, the sub-series characterized in that the specific portion of the subject's vasoactive response is the portion sensitive to quantifying a reduction in cerebrovascular reactivity.

21 Claims, 7 Drawing Sheets

(51) Int. Cl.
  *A61B 5/055* (2006.01)
  *A61B 5/0205* (2006.01)
  *A61B 5/145* (2006.01)
(52) U.S. Cl.
  CPC ............ *A61B 5/055* (2013.01); *A61B 5/0205* (2013.01); *A61B 5/14542* (2013.01); *A61B 5/4836* (2013.01); *A61B 2576/026* (2013.01)
(58) Field of Classification Search
  CPC ....... A61B 5/4836; A61B 5/026; A61B 5/055; A61B 5/4064; G06T 2207/10088; G06T 2207/30016; G06T 2207/30104; G06T 7/0012; G06T 7/11; G06T 7/38
  See application file for complete search history.

(56) References Cited

FOREIGN PATENT DOCUMENTS

| WO | WO-2004073779 A2 | 9/2004 |
|----|------------------|--------|
| WO | WO2007/012197 | 2/2007 |
| WO | WO2011/143751 | 11/2011 |
| WO | WO2012/130248 | 10/2012 |
| WO | WO2013/030743 | 3/2013 |
| WO | WO-2013138910 A1 | 9/2013 |
| WO | WO-2014194401 A1 | 12/2014 |

OTHER PUBLICATIONS

Written Opnion on corresponding PCT application (PCT/CA2015/000274) from International Searching Authority (CIPO) dated Jul. 17, 2015.
Nadkarni et al. Usage of fMRI for pre-surgical planning in brain tumor and vascular lesion patients: task and statistical threshold effects on language lateralization.: Neuroimage Clin. Dec. 24, 2014; 7:415-23. doi: 10.1016/j.nicl.2014.12.014.eCollection 2015. PMID: 25685705; http://www.ncbi.nlm.nih.gov/pmc/articles/PMC4310930/pdf/main.pdf.
Sam et al. "Assessing the Effect of Unilateral Cerebral Revascularisation on the Vascular Reactivity of the Non-Intervened Hemisphere: A Retrospective Observational Study." BMJ Open 5.2 (2015): e006014. PMC. Published: Feb. 11, 2015; http://www.ncbi.nlm.nih.gov/pmc/articles/PMC4325130/pdf/bmjopen-2014-006014.pdf.
Sobczyk et al. Assessing cerebrovascular reactivity abnormality by comprision to a reference atlas.: Journal of Cerebral Blood Flow & Metabolism [serial online]. Feb. 2015; 35(2):213-220. Academic Search Research & Development, Ipswich, MA.; https://search.ebscohost.com/login.aspx?direct=true&db-asr&AN=100713008.
Spano et al. "CO2 blood oxygen level-dependent MR mapping of cerebrovascular reserve in a clinical population: safety, tolerability, and technical feasibility." Radiology. Feb. 2013; 266(2):592-598. doi: 10.1148/radiol.12112795. Epub Nov. 30, 2012; http://pubs.rsna.org/doi/pdf/10.1148/radiol.12112795.
Terashima et al. "Noninvasive assessment of coronary vasodilation using magnetic resonance angiography." J Am Coll Cardio. 2005; 45(1); 104-110. doi: 101016/j.jacc.2004.09.057. http://content/onlinejacc.org/article.aspx?articleid=1136202.
Wise et al. "Measurement of OEF and Absolute CMRO2: MRI-Based Methods Using Interleaved and Combined Hypercapnia and Hyperoxia." NeuroImage 83 (2013): Dec. 2013, pp. 1-31. http://www.ncbi.nlm.nih.gov/pmc/articles/PMC4151288/pdf/emss-60178.pdf.
Ashburner, John, and K. Friston. "Multimodal image coregistration and partitioning—a unified framework." Neuroimage 6.3 (1997): 209-217.
Balucani, Clotilde, et al. "Cerebral hemodynamics and cognitive performance in bilateral asymptomatic carotid stenosis." [Abstract Only] Neurology 79.17 (2012): 1788-1795.
Cox, Robert W. "AFNI: software for analysis and visualization of functional magnetic resonance neuroimages." Computers and Biomedical research 29.3 (1996): 162-173.
Fierstra, Jorn, et al. "Severely impaired cerebrovascular reserve in patients with cerebral proliferative angiopathy." Journal of Neurosurgery: Pediatrics 8.3 (2011): 310-315.
Fierstra, Jorn, et al. "Non-invasive accurate measurement of arterial PCO 2 in a pediatric animal model." [Abstract Only] Journal of clinical monitoring and computing 27.2 (2013): 147-155.
Guimond, Alexandre, Jean Meunier, and Jean-Philippe Thirion. "Average brain models: A convergence study." Computer vision and image understanding 77.2 (2000): 192-210.
Han, Jay S., et al. "BOLD-MRI cerebrovascular reactivity findings in cocaine-induced cerebral vasculitis." Nature Reviews Neurology 4.11 (2008): 628.
Han, Jay S., et al. "Measurement of cerebrovascular reactivity in pediatric patients with cerebral vasculopathy using blood oxygen level-dependent MRI." Stroke 42.5 (2011): 1261-1269.
Mikulis, David J., et al. "Preoperative and postoperative mapping of cerebrovascular reactivity in moyamoya disease by using blood oxygen level—dependent magnetic resonance imaging." [Abstract Only] Journal of neurosurgery 103.2 (2005): 347-355.
Seitz, R. J., et al. "Accuracy and precision of the computerized brain atlas programme for localization and quantification in positron emission tomography." Journal of Cerebral Blood Flow & Metabolism 10.4 (1990): 443-457.
Mark, Clarisse I., et al. "Precise control of end-tidal carbon dioxide and oxygen improves BOLD and ASL cerebrovascular reactivity measures." Magnetic resonance in medicine 64.3 (2010): 749-756.
Sobczyk, Olivia, et al. "A conceptual model for CO2-induced redistribution of cerebral blood flow with experimental confirmation using BOLD MRI." Neuroimage 92 (2014): 56-68.
Tzeng, Yu-Chieh, et al. "Assessment of cerebral autoregulation: the quandary of quantification." American Journal of Physiology-Heart and Circulatory Physiology 303.6 (2012): H658-H671.
Webb, Jocasta, et al. "Automatic detection of hippocampal atrophy on magnetic resonance images." [Abstract Only] Magnetic Resonance Imaging 17.8 (1999): 1149-1161.
White, Nicole D. "Increasing Naloxone Access and Use to Prevent Opioid Overdose Death and Disability." American journal of lifestyle medicine 13.1 (2019): 33-35.
The FIL Methods Group. "Statistical Parametric Mapping." The Wellcome Centre for Human Neuroimaging (UCL), Functional Imaging Laboratory, Oct. 1, 2014, URL: https://www.fil.ion.ucl.ac.uk/spm/.

Effect of Δ PaCO$_2$ on CVR In hypercapnic range
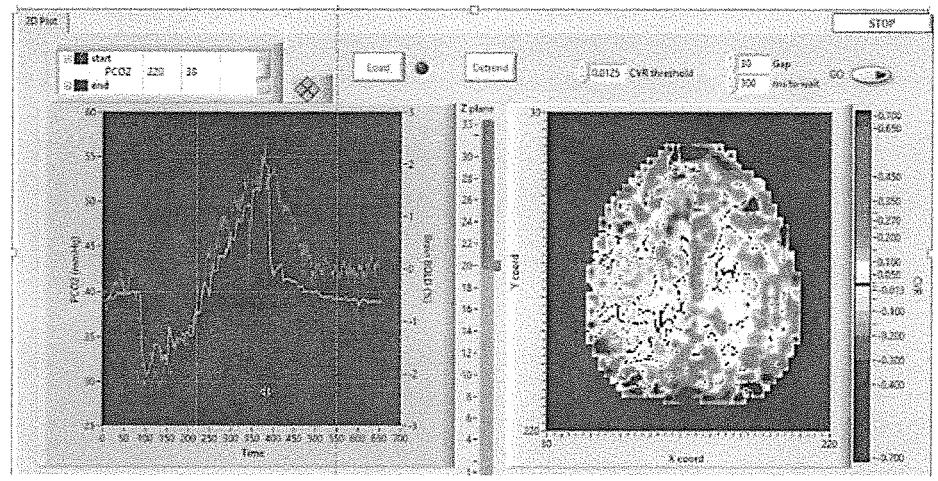
Noise in BOLD signal:
- the smaller the Δ PETCO$_2$ the greater the noise
- can resolve CVR over range of only 2 mmHg
Patient 3
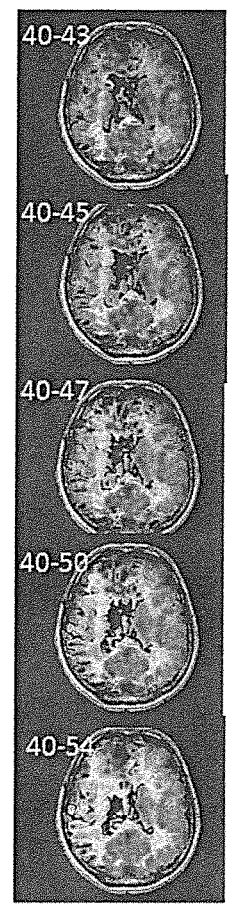
Figure 3a
Figure 3b

IMAGING REDUCTIONS IN CEREBROVASCULAR REACTIVITY

CROSS-REFERENCE TO RELATED APPLICATION

The present application is a continuation of U.S. patent application Ser. No. 14/614,310, filed Feb. 4, 2015, now abandoned, the disclosure of which is hereby incorporated by reference as if set forth in full herein, and which claims benefit of priority from U.S. Provisional Application No. 61/984,617, filed Apr. 25, 2014.

FIELD OF THE INVENTION

The present invention relates a system and method for locating and assessing pathophysiological changes in cerebrovascular reactivity.

BACKGROUND OF THE INVENTION

Cerebrovascular reactivity (CVR) is the change in cerebral blood flow (CBF) in response to a change in a vasoactive stimulus. Paradoxical reductions in the amplitude of CBF response to vasodilatory stimulation ('steal') are associated with vascular pathology. However, vascular pathology may exist without overt steal. A sensitive measure of abnormal CVR and vascular physiology requires a comprehensive conceptual model linking vascular pathology and changes in blood flow and a system of data analysis capable of detecting changes in regional CBF.

SUMMARY OF THE INVENTION

The inventors have discovered a system for detecting an abnormality in a subject's cerebrovascular response to a vasoactive stimulus. The system includes a system for generating a step change (step), or a series of increments, or decrements (Ramp) in the vasoactive stimulus (an SVS) and an imaging system (an IS) that provides sufficient spatial and time resolution for analyzing a response to a step and/or Ramp stimulus. The vasoactive response preferably constitutes a surrogate measure of blood flow in a region of interest (ROI) of the subject's brain. The system includes a computer for implementing an algorithm for analyzing the signal responses, as a function of the Ramp (increment or decrement) change for (or optionally as a function of time following a step change in the vasoactive stimulus). The algorithm including program code for analyzing a specific portion of the vasoactive response to the vasoactive stimulus corresponding to a to sub-range of increments and/or decrements of stimuli within the full range of the vasoactive stimulus, the sub-range characterized in that is more sensitive to identifying reductions in vascular reactivity in the ROI. The inventors have discovered that using the response signals corresponding to this sub-range of increments and/or decrements in the vasoactive stimulus, for example, to compute a value representing a quantitative measure of cerebrovascular reactivity for the ROI, is more sensitive to discriminating a reduction in cerebrovascular reactivity for the ROI than making the determination from the collection of responses over the full range of the stimulus. In general, the value is used to quantify the amount of change in a surrogate measure of blood flow that is associated with a change in the vasoactive stimulus.

The value can be used to construct a CVR map by visually depicting the value or an interpretive score corresponding to the value, in a precise anatomical location on an image of the ROI. For example, the value or score may be color coded and/or illustrated topographically. Optionally, the value or score may be statistically interpreted on an image of the ROI to provide a degree of statistical confidence that the value reflects a pathophysiological change in CVR/blood flow. For example, by computing, on a ROI by ROI basis, for at least one ROI, at least one score per ROI, that evaluates the extent to which the value deviates from the range of values representing the CVR for the ROI in a healthy cohort (e.g. individuals without neurological disease for whom a CVR per ROI is computed using the response signals corresponding to the same sub-range of increments and/or decrements in the vasoactive stimulus), one can obtain a degree of statistical confidence that this computed value represents a pathophysiological reduction in CVR for the ROI, that is, being outside of the normal range of CVR. This score can be color coded and represented on a ROI by ROI basis, on a CVR map of the subject's brain. Optionally, the ROI is a voxel within a large ROI that is composed of a set of voxels. The inventors have applied this analysis to one or more ROIs, on a voxel by voxel basis, to obtain a set of respective computed values, and respective scores for each voxel in ROI, and when the voxels are colored by a color corresponding to the magnitude of the score, resulting in a CVR map.

Thus, according to one aspect the invention is directed to a system for detecting an abnormality in a subject's cerebrovascular response to a vasoactive stimulus in at least one region of interest (ROI) of the subject's brain, as depicted in FIG. 7. The system includes:

(A) a system for generating the vasoactive stimulus (SVS);

(B) an imaging system (IS) characterized in that it provides sufficient spatial and time resolution for analyzing a vasoactive response to a step change or series of increments and/or decrements in the vasoactive stimulus, the vasoactive response preferably constituting a surrogate measure of blood flow in the at least one ROI;

(C) a computer for implementing an algorithm for analyzing the vasoactive response to a series of increments and/or decrements in a vasoactive stimulus, the algorithm including program code:

(a) for computing at least one value representing a quantitative measure of cerebrovascular reactivity for the ROI, wherein the at least one value is obtained for a specific portion of the vasoactive response in the ROI, the specific portion of the response corresponding to a to sub-range of increments and/or decrements in the vasoactive stimulus within the full range of the vasoactive stimulus, the sub-range characterized in that it is sensitive to quantifying a reduction in cerebrovascular reactivity; and optionally (b) computing on a ROI by ROI basis (for at least one ROI), at least one score (per ROI) adapted for interpreting the at least one value.

The score is optionally adapted to visually represent the value and its location in a depiction of the brain or the ROI. The value is optionally the CVR for the selected sub-range of increments and/or decrements in the vasoactive stimulus within the full range of the vasoactive stimulus. Optionally, the score is adapted to grade the amplitude of the CVR and its course as a function of the changes in the vasoactive stimulus such as the ramp changes in carbon dioxide partial pressure ($PCO_2$ or $PaCO_2$). Optionally, a visual representation such as a color, of the value of the interpretive score is mapped onto a depiction of the brain to provide a visual depiction where each voxel or ROI is associated with its score. Optionally, the score is computed on a voxel by voxel basis and is, for example, geared to visually depicting the amplitude of the CVR on an anatomical image of a slice of the brain composed of a set of voxels constituting the ROI.

Optionally, the score quantifies the extent to which that the at least one value deviates from a range of that value computed for corresponding ROI in a control cohort, wherein the score reflects the statistical confidence that the at least one value computed as in (a) represents a reduction in CVR.

The sub-range of the vasoactive stimulus is characterized in that it is more sensitive to quantifying a reduction in cerebrovascular reactivity relative to a quantitative measure of CVR computed using an alternative set of response signals, the alternative set of response signals corresponding to at least one of a full range of the vasoactive stimulus or a range of the vasoactive stimulus for which the corresponding set of response signals better identifies a reduced CVR for the ROI than the set of response signals corresponding to a full range of the vasoactive stimulus. Optionally, the algorithm includes program code for identifying a sub-range of the vasoactive stimulus that is sensitive to quantifying a reduction in cerebrovascular reactivity. Alternatively or additionally, the sub-range of the vasoactive stimulus for which the at least one value is computed includes a portion of the vasoactive stimulus for which the signal to noise ratio is best adapted to discriminate a reduction in CVR. For example if, the series of increments and/or decrements in a vasoactive stimulus is a series of target end tidal concentrations of carbon dioxide, the portion of vasoactive stimulus in question may be the increments and/or decrements corresponding to the highest 4 to 6 mm of Hg in the partial pressure of carbon dioxide (provided the upper range of the stimulus is one in which stimulated blood flow demand for the ROI sufficiently exceeds the blood flow supply to result in a relative distribution of blood flow in favor of healthy vessels at the expense of vessels that have a reduced CVR).

Optionally, the ROI is a voxel within a larger ROI. Accordingly, the at least one value and the at least one score is a set of respective values and corresponding scores computed on a voxel by voxel basis for a series of voxels within the larger ROI.

Optionally, these scores are color coded and represent the ROI on a CVR map.

Optionally, the series of increments and/or decrements in a vasoactive stimulus is a series of target end tidal concentration of carbon dioxide (end tidal concentrations of carbon dioxide are deemed reliable surrogate measures of the arterial partial pressure of carbon dioxide).

Optionally, the algorithm includes program code for computing at least one CVR for the specific portion of the response identified in step (a) and program code for determining whether the CVR that is computed for this specific portion of the response represents a reduction in CVR. For example, the algorithm may include program code for identifying a stimulus range or time range of the at least one portion of the vasoactive response for which the signal to noise ratio is sufficient to discriminate a reduced CVR within a relatively broader range of the vasoactive response, the analysis of which would result in a greater CVR value. For example, the algorithm may include program code for identifying at least one portion of response that satisfies at least one of the following conditions:

i) the stimulus range is sufficiently large to identify a reduced CVR (at least to compute a slope or a tangent to the response curve);

ii) the upper range of the stimulus is one in which stimulated blood flow demand sufficiently exceeds the blood flow supply to result in a relative distribution of blood flow in favor of healthy vessels at the expense of vessels that have a reduced CVR.

Step (a) may be executed on a voxel by voxel basis and/or for the ROI as a whole.

Optionally, the system of generating the vasoactive stimulus is an end tidal forcing system or a $CO_2/O_2$ rebreathing circuit, virtual (see WO/2013/138910) or physical (see WO/2004/073779). Optionally, the system of targeting a step increase or decrease in the arterial partial pressure of carbon dioxide (e.g. a jump of 5 to 10 mm of Hg in one breath) or a series increments/decrements in the end tidal partial pressure of carbon dioxide may be done with a controller for controlling a gas blender which employs a prospective model, a feedback model or a combination of both (see our published application WO/2014/194401) to determine how much gas to deliver to the subject at each interval e.g. in each breath to attain a target end tidal partial pressure of carbon dioxide for the interval. These control systems can be used to simultaneously maintain desired partial pressure of oxygen.

Optionally, the system for generating the vasoactive stimulus comprises an apparatus for controlling an amount of carbon dioxide ($CO_2$) in a subject's lung to attain a series of targeted end tidal partial pressures of $CO_2$ ($PetCO_2^T$), as depicted in FIG. 7. The apparatus may include:

(a) a gas delivery device;

(b) a control system for controlling the gas delivery device, wherein the control system is programmed to target a series of $PetCO_2^T$ values for a series of respective intervals, the series of $PetCO_2^T$ values comprising at least one of a set of $PetCO_2^T$ increments and a set of $PetCO_2^T$ decrements, the control system including means for:

a. Obtaining (e.g. by pre-programming, by electronic communication or by providing input via an input device) input of a series of logistically attainable $PetCO_2^T$ values for the series of respective intervals; and b. Determining an amount of $CO_2$ required to be inspired by the subject in an inspired gas to target the $PetCO_2^T$ for a respective interval;

c. Controlling the amount of gas $CO_2$ in a volume of gas delivered to the subject in a respective interval to target the respective $PetCO_2^T$ for the interval.

Optionally, at least one of:

(a) the respective sizes of the at least one of the set of $PetCO_2^T$ increments and the set of $PetCO_2^T$ decrements and the size of the respective intervals; and (b) the time over which the response is measured and the range of the vascular response; is predetermined to reveal a dose response to at least one of the set of $PetCO_2^T$ increments and the set of $PetCO_2^T$ decrements.

Optionally, each interval is a respective breath [i].

Optionally, the vasoactive response is a vasodilatory response to a set of $PetCO_2^T$ increments. The set of logistically attainable $PetCO_2^T$ values produces a range of a vasodilatory stimulus sufficient to reveal a reduced CVR for each respective ROI of interest, the series of intervals is selected to satisfy a condition, the condition defined by attainment of at least a minimum increment in the vasodilatory response to an increment in the subject's end tidal partial pressure $CO_2$ (optionally the series of $PetCO_2^T$ values for the series of respective intervals also revealing the time course of at least one of a partial range of a vasodilatory response and a full range of a vasodilatory response).

Optionally, the set of increments in $PetCO_2^T$ for the series of respective intervals is predetermined to produce one to two time constants in the progress of the vasoactive response in a respective interval.

Optionally, the at least one set of increments in $PetCO_2^T$ for the series of respective intervals is predetermined to produce two to three time constants in the progress of the vasoactive response in a respective interval.

Optionally, the imaging system is an MRI scanner. A standardized set of MR imaging protocols is used to generate a set of hemodynamic response signals corresponding to each of the increments and/or decrements in vasoactive stimulus (for example, each increment and/or decrement in a set of target end tidal partial pressures of carbon dioxide ($PetCO_2^T$). The response signals are a surrogate measure of blood flow. For example, the images optionally represent a change in a blood oxygen level dependent (BOLD) magnetic resonance imaging (MRI) response to a set of targeted incremental increases in a subject's end tidal $PCO_2$ ($P_{ET}CO_2$), the vascular response values representing a change in BOLD MRI signal ($\Delta S$), in response to a standardized increase in the $P_{ET}CO_2$ ($CVR=\Delta S/\Delta P_{ET}CO_2$). The stimulated rise and/or decline is preferably implemented at a controlled rate (which may include a sinusoidal pattern), and optionally at a constant rate (i.e. the size of the increments/decrements are equal and intervals between them are the same). Optionally, the constant rate of increase is sufficiently slow to reveal at least one to two time constant in progress of the response, optionally two to three time constants in the progress of the response. It is generally understood that the time constants of the response vary throughout the brain and may vary even more in areas with vascular pathology. By changing the vasoactive stimulus a constant rate, a steady state relationship between $PCO_2$ and cerebral blood flow (CBF) is approached. There is a trade off between the time to reach CBF equilibrium and the time taken for the scan which is limited due to subject comfort, drift of the MRI signal over time, and cost for MRI time. At any rate of rise, the slope $\Delta S/\Delta PCO_2$ (or, CVR) will be the same so coming to equilibrium is not crucial.

Optionally, a CVR is computed for each of a series of specific portions of the vasoactive response, which portions are collectively sufficient to identify at least one of the following: (A) a reduced CVR per voxel in the ROI; (B) a CVR which is or approximates a lowest CVR for the voxel, the CVR preferably computed for a portion of the response in which stimulated blood flow demand sufficiently exceeds the blood flow supply to identify a reduced CVR in the ROI. In practical terms, selecting a range of the vasoactive stimulus at which the blood flow sufficiently exceeds the demand occurs at the upper end of the stimulus range (the higher the $CO_2$ the greater the tendency to cause steal between vascular territories of unequal vasodilatory reserve; therefore the responses at the highest $PCO_2$ range will be the most sensitive in picking up steal. Also, whereas vascular territories with reduced reserve may be able to increase their flow at small increments of $PCO_2$ from resting values, at higher $PCO_2$ levels, they change direction and begin to reduce their flow with each increment in $pCO2$). For example, a range of the stimulus which is either 7 to 12, 7 to 13, 8 to 12, 8 to 13, 8 to 14, 9 to 13, 9 to 14, 9 to 15, 10 to 15 or 10 to 16 mm of Hg above a baseline for the subject are each likely, and in the order presented, each increasingly more likely, to identify a portion of the response in which stimulated blood flow demand sufficiently exceeds the blood flow supply to identify a reduced CVR in the ROI.

Optionally, a CVR is computed for at least one portion of the vasoactive response (optionally each of a series of specific portions of the vasoactive response), which portion(s) is/are individually/collectively sufficient to yield at least one of the following: (A) a score representing a negative CVR per ROI (B) a score corresponding to the lowest CVR for the ROI; and (C) a score identifying whether or not (and/or the extent to which) a CVR can be computed for the ROI which is less than a second CVR which is the lowest positive CVR for the ROI. The CVR(s) is preferably computed for a portion of the response in which stimulated blood flow demand sufficiently exceeds the blood flow supply to identify a reduced CVR.

Optionally, the algorithm includes program code for: a) fitting a polynomial to the entire vasoactive response (which corresponds to a full range of the vasoactive stimulus selected for analysis); b) computing a first derivative of the polynomial; and c) identifying negative slopes corresponding to a specific portion of the vasoactive response for which the signal to noise ratio is sufficiently high to discriminate a reduced (e.g. a negative) CVR within a relatively broader range of the vasoactive response for which the CVR may be positive.

Optionally, in order to score a CVR relative to a control cohort, an imaging system and a standardized set of imaging protocols are used to generate for members of a group of control subjects, a set of vascular response signals depicting a non-pathological vascular response, in at least one common ROI of each control subject's brain, wherein the vascular response is a reaction to a controlled vasoactive stimulus, and wherein the vascular response is quantifiable from images corresponding to the vascular response signals, on an ROI-by-ROI basis (optionally on a voxel-by-voxel basis), in the form of response value per voxel for the particular sub-range of the stimulus employed. A standardized algorithm is used to co-register the respective control subject images to a standardized space based on a set of anatomic landmarks. A computer computes, for the co-registered set of control subject images, on a ROI by ROI basis (e.g. a voxel by voxel basis), a mean and standard deviation of the vascular response values for voxels corresponding to the at least one ROI to define, for the control group as a whole, a set of statistical values respectively associated an ROI (optionally, for each voxel constituting the ROI). The imaging system and standardized set of imaging protocols is used to compute a value representing a quantitative measure of cerebrovascular reactivity for the ROI for a subject in need of an assessment of a vascular response, employing the standardized vasoactive stimulus by scoring the respective responses for the ROI e.g. individual voxels in the ROI (or for the ROI as a whole), relative to the respective corresponding computed means and standard deviations, using z values. Optionally, this method further comprises the step of color-coding the z values and mapping the color-coded values back onto an anatomical representation of the standardized space to produce a z map. Optionally, the images represent the changes in blood oxygen level dependent (BOLD) magnetic resonance imaging (MRI) response to a targeted increase in a subject's end tidal $PCO_2$ ($P_{ET}CO_2$), the vascular response values representing, for example, a change in BOLD MRI signal ($\Delta S$), in response to a standardized increase in the $P_{ET}CO_2$ ($CVR=\Delta S/\Delta P_{ET}CO_2$) scored in terms of the standard deviation of the CVR for the corresponding voxel in the healthy cohort, that is, its z score. CVR which is a measure of the slope of the line can be computed only from the respective response values corresponding to lowest and higher increments in P$_{ET}$CO$_2$ or using a linear regression analysis based on all of the response values obtained for a selected sub-range of the vasoactive stimulus, for example, by fitting a least squares regression line to the data.

Optionally, the set of control subjects are selected on the basis that they report being free of neurological disease.

Optionally, the control subjects are matched for a parameter that is appropriate for the condition being examined in a patient. The term patient is used broadly to define a subject being tested with reference a selected control population.

Optionally, the set of control subjects are matched for at least one of age and gender.

In another aspect, the invention is directed to a computer program product for implementing an algorithm for analyzing the vasoactive response to a series of increments and/or decrements in a vasoactive stimulus, the algorithm including program code:

(a) for computing at least one value representing a quantitative measure of cerebrovascular reactivity for the ROI, wherein the at least one value is obtained for a specific portion of the vasoactive response in the ROI, the specific portion of the response corresponding to a to sub-range of increments and/or decrements in the vasoactive stimulus within the full range of the vasoactive stimulus, the sub-range characterized in that it is sensitive to quantifying a pathological reduction in cerebrovascular reactivity; and optionally (b) computing on a ROI by ROI basis (for at least one ROI), at least one score (per ROI) adapted for interpreting the at least one value.

The score is optionally adapted to visually depict the value. The value is optionally the CVR for the selected sub-range of increments and/or decrements in the vasoactive stimulus within the full range of the vasoactive stimulus. Optionally, the score is adapted to grade the amplitude of the CVR. Optionally, the value or interpretive score is visually depicted on an image of the ROI. Optionally, the score is computed on a voxel by voxel basis and is, for example, geared to visually depicting the amplitude of the CVR on an anatomical image of a slice of the brain composed of a set of voxels constituting the ROI.

Optionally, the score quantifies the extent to which that the at least one value deviates from a range of that value computed for corresponding ROI in a control cohort, wherein the score reflects the statistical confidence that the at least one value computed as in (a) represents a reduction in CVR.

The aforementioned computer program product optionally includes program code for controlling a gas delivery device, the gas delivery device adapted for controlling an amount of carbon dioxide (CO$_2$) in a subject's lung to attain a series of targeted end tidal partial pressures of CO$_2$ (PetCO$_2^T$) for a series of respective intervals, including program code for:

a. Obtaining input of a series of logistically attainable PetCO$_2^T$ values for the series of respective intervals; and b. Determining an amount of CO$_2$ required to be inspired by the subject in an inspired gas to target the PetCO$_2^T$ for a respective interval; and c. Controlling the amount of gas CO$_2$ in a volume of gas delivered to the subject in a respective interval to target the respective PetCO$_2^T$ for the interval; and optionally d. maintaining the subject's end tidal PO$_2$ at a constant level (i.e. within 20 mmHg of a baseline level for the subject)

The invention is also directed to an IC chip for implementing an algorithm as described herein (optionally a programmable IC chip) and optionally for also controlling a gas delivery device as aforesaid.

According to another aspect, the invention is directed to a neuro-imaging assessment method in aid of diagnosing at least one of the existence, location, deterioration and amelioration of a brain disorder associated with abnormal vascular reactivity, for example a cerebrovascular disorder.

The neuro-imaging assessment protocol of the present invention, including any permutations of the steps defined above or below, enables images to be produced from which such diagnostic assessments may be carried out and/or confirmed. According to one embodiment the invention, we describe a novel cerebrovascular reactivity assessment protocol for producing a reference atlas, for example an atlas of non-pathological cerebrovascular reactivity, wherein the CVR values computed for the reference atlas are specific to a sub-range of the response stimulus that is selected for discriminating a reduction in cerebrovascular reactivity, a sub-range particularly suitable to identify steal.

Accordingly in a further embodiment, the invention provides for a method and for the use such an atlas of non-pathological cerebrovascular reactivity to produce neuro-imaging results from which a subject in need of assessment of abnormal cerebrovascular reactivity can be assessed for the abnormality. The method optionally comprises producing a reference atlas and comparing voxel by voxel (adjacent voxels may be taken in account in assigning voxel values in give a region of interest according to standardized algorithms well known to persons in the field) test vascular response values of a patient to the corresponding reference atlas value by scoring those values, preferably in a manner that accounts for relative departure of the test value from a quantity describing a characteristic value (e.g. mean/SD for normal distributions of value or normal distributions of log values) such as to account for the variability or distribution of the control values.

According to another aspect the invention is directed to a diagnostic tools in the form of a neuro-image and other visual depictions such as graphs derived from such images that incorporate statistical transformations of MR signals generated in response to a sub-range (as described above) of the response stimulus that is selected for discriminating a reduction in cerebrovascular reactivity, optionally one or more step changes or a set of increments/decrements in end-tidal PCO$_2$. According to one embodiment the invention is directed to a cerebrovascular reactivity response map in the form a z map.

For example, according to one embodiment the invention is directed to a diagnostic tool comprising color-coded z values mapped onto an anatomical representation of a standardized 3D map of at least one region of interest (ROI) of the brain, the z values and 3D map characterized in that a standardized set of MR imaging protocols are employed to generate for members of a group of control subjects, a set of CVR response signals corresponding to a sub-range of the response stimulus that is selected for discriminating a reduction in cerebrovascular reactivity, wherein the response signals depict a non-pathological CVR response, in at least one common ROI of each control subject's brain, wherein the CVR response is a reaction to a standardized vasoactive stimulus, and wherein the CVR response is quantifiable from images corresponding to the response signals, on a voxel-by-voxel basis, in the form of CVR response value per voxel; and wherein a) a standardized algorithm is used to co-register the respective control subject images to a standardized space based on a set of anatomic landmarks;

b) a computation, for the set of control subjects, on a voxel by voxel basis, of a mean and standard deviation of the CVR response values for voxels corresponding to the at least one ROI is used;

c) the MR scanner and the standardized set of MR imaging protocols is used to measure a CVR response for a subject in need of an assessment of an abnormality in CVR, employing the standardized vasoactive stimulus (a sub-range of the response stimulus that is selected for discriminating a reduction in cerebrovascular reactivity, optionally one or more step changes or a set of increments/decrements in end-tidal $PCO_2$) by scoring the respective responses for individual voxels in the at least one ROI, relative to the computed mean and standard deviation, using z values.

Optionally, z values can be generated for test subjects that are based on a measurement of a plurality of CVR test values, on a voxel by voxel basis, for each respective control subject. Multiple CVR values per control subject are obtained from a plurality of imaging tests generated using a standardized stimulus and therefore reflect expected test/retest variability in CVR measurements. The successive tests are preferably conducted on different days and optionally at different times of day, such that the plurality of variant values reflect primarily the inevitable variations corresponding to normal variations in physiology and in the technology (even despite using a single scanner), over time. The different values may also reflect in minor part differences due to other categories influences (e.g. unidentified sources of small variation or, identifiable sources of small variation of the type not generally subject to practical control).

The standard CVR atlas may reflect this retest value in the means and standard deviation per voxel. Alternative the probative value of such re-test values can be accentuated by generating a specialized reference atlas (an Interval Difference atlas) in which the control group ROI or voxel means and standard deviations are calculated with respect to intra-subject differences e.g. say between the two test values for a subject which are subtracted from one another. The intra-subject test/re-test variability, however quantified or accounted for, both from an intra-control subject perspective and across a group of control subjects, is important for assessing a patients change in CVR per voxel against a backdrop of normal re-test variability.

These so-called Interval Difference (ID) variations may be used to compute ID Z values for a given control or diseased subject, and for creating for the group of subjects, an atlas of test-retest value differences, on a voxel by voxel basis. This enables an attribution of the statistical probability that changes in CVR to true interval change in pathophysiology. Optionally resulting ID-Z values may be as reference maps to monitor progression of the disease over time or responses to treatment.

BRIEF DESCRIPTION OF THE DRAWINGS

FIG. 1 includes CVR maps. Demand does not exceed supply so there is no steal.

FIG. 2 also includes CVR maps. FIG. 2 shows that in a patient with severe inflow limitation such as this patient with complete carotid artery occlusion, (a) the degree of steal increases with increasing $PETCO_2$; (b) at low increases in $PCO_2$ many voxels that show steal at high $PCO_2$ have positive flow at initial increments in $PCO_2$ in other words, in voxels with steal, the signal vs. $PETCO_2$ curve is concave downwards (c) mall increments of $PETCO_2$ make obvious differences in distribution and intensity of steal.

FIG. 3a shows a graph of $PCO_2$ and BOLD signal over time and a corresponding CVR map. FIG. 3b illustrates a series of CVR maps.

DETAILED DESCRIPTION OF PREFERRED EMBODIMENT

The description herein contemplates a variety of suitable criteria for revealing a reduced CVR. Each has useful discriminatory ability for initial test purposes. For example, a negative CVR may constitute, a priori, a useful indicator of impaired CVR for a voxel. However, for some ROIs (e.g. voxels) this measure alone might prove to be a false indicator of impaired reactivity as revealed by comparing the value with a corresponding value computed for the same sub-range of increments in stimulus in a normal cohort. Scoring the value, and quantifying the extent to which that the value deviates from a range of that value computed for corresponding ROI in a control cohort provides a enhanced level of discriminatory ability, the score thus reflecting the statistical confidence that the value represents a pathological reduction in CVR.

In the disclosure herein, the term Ramp sequences are used to refer to increments or decrements in carbon dioxide partial pressure ($PaCO_2$). One method for producing Ramp sequences is described in our co-pending U.S. patent application Ser. No. 14/398,034 (the '034 application) for an invention entitled A NEW METHOD AND APPARATUS TO ATTAIN AND MAINTAIN TARGET ARTERIAL BLOOD GAS CONCENTRATIONS USING RAMP SEQUENCES (see also our publication Sobczyk 0, et al. A conceptual model for $CO_2$-induced redistribution of cerebral blood flow with experimental confirmation using BOLD MRI. Neuroimage. 2014 May 15; 92:56-68).

The disclosure of '034 application also describes how to independently target and maintain a particular partial pressure of oxygen. This can also be done by well know methods of end tidal forcing.

A method of stastically scoring CVR values and a method producing a CVR atlas to facilitate such scoring is described in our U.S. Provisional Patent Application No. 61/984,617 filed Date: Apr. 25, 2014 for an invention entitled "IMAGING ABNORMALITIES IN VASCULAR RESPONSE" (see also our publication: Sobczyk O, et al. Assessing cerebrovascular reactivity abnormality by comparison to a reference atlas. J Cereb Blood Flow Metab. 2015 February; 35(2):213-20)

The disclosures of all aforementioned patent applications and scientific publications are hereby incorporated in their entirety by reference.

Figure 1:
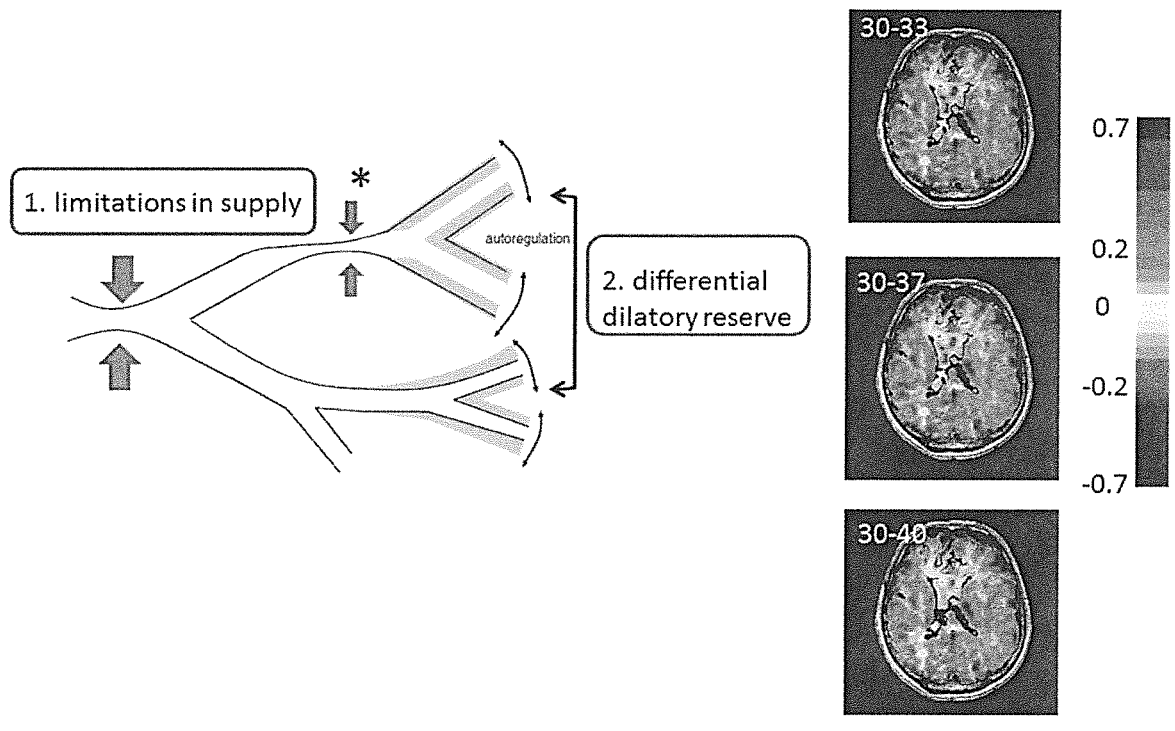
FIG. 1 is a diagrammatic representation of how CVR is affected in a hypocapnic range of a $PCO_2$ stimulus in a patient with R carotid artery stenosis.
Figure 2:
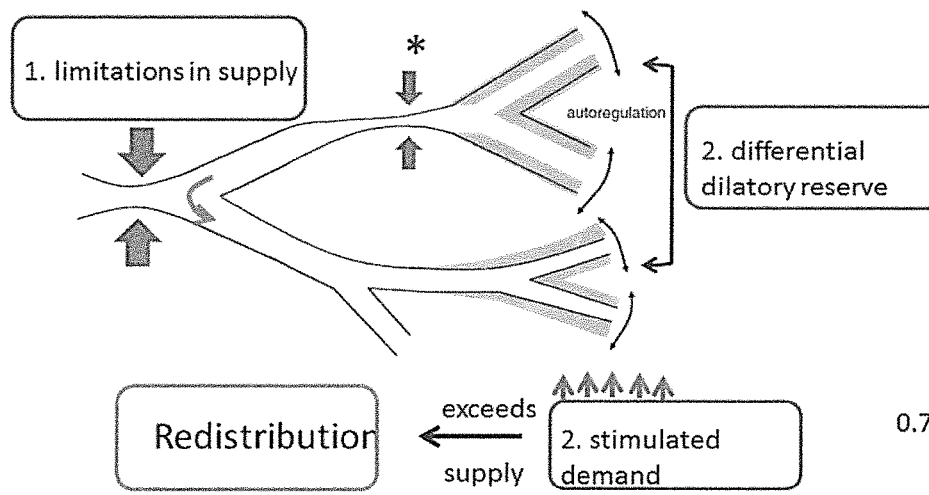
FIG. 2 is a diagrammatic representation of how CVR is affected in a hypercapnic range of a $PCO_2$ stimulus in the same patient with R carotid artery stenosis.
Figure 2:
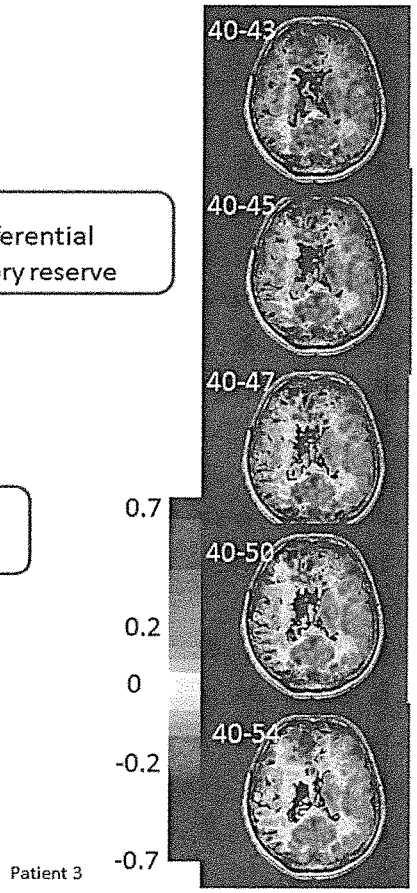

In the hypercapnic range, the increase in demand resulting from the ramping up of $P_{ET}CO_2$ and thus $PaCO_2$ results in progressive steal. The higher the $\Delta PaCO_2$, the greater the steal. FIG. 2 shows that 1. The hypercapnic region is different from the hypocapnic in that vasodilatation begins the competition between inflow and steal.
2. Small changes in $PaCO_2$ result in obvious different degrees and distribution of steal. No method that uses breath-hold or fixed inspired $PCO_2$ (carbogen) can target $PaCO_2$ within even 3-5 mmHg. Total rebreathing with oxygen supplementation to maintain normoxia, or computerized targeting such as prospective targeting using sequential gas delivery, or end-tidal forcing, may target within 2 mmHg with variable consistency. However, due to continuous ramping change, all $PaCO_2$ values in the range are obtained and precise A $PaCO_2$ can be accessed for analysis.
3. Methods that target a single $P_{ET}CO_2$ (breath holding, fixed inspired $PCO_2$, DEF, prospective targeting) take variable durations of time to attain a target level and further variable durations to reach a steady state such that any S can be related to $PaCO_2$. This time to equilibration is considerable and variable, but only follows on the attainment of a steady $PaCO_2$. No method other than DEF and RA can sustain a specific target level. With the Ramp, all values are at the same near equilibrium state; in any case the $\Delta S/\Delta P_{ET}CO_2$ will be the same as the steady state.

FIGS. 3a and 3b (FIG. 3) illustrate that small $\Delta PaCO_2$ as occur in step changes with fixed inspired $CO_2$ and breath-holding result in noisy data and unreliable and poorly repeatable CVR. However, the $PaCO_2$ effect is stronger than the signal noise. Ramp sequences enable the generation of a large amount of signal data to regress against the $PaCO_2$. This is not available with square wave data due to the unknown dynamic effect resulting in "intermediate" S values while coming to equilibrium but attributed to the equilibrium $P_{ET}CO_2$. FIG. 3 also illustrates the noise in BOLD signal.

Figure 4:
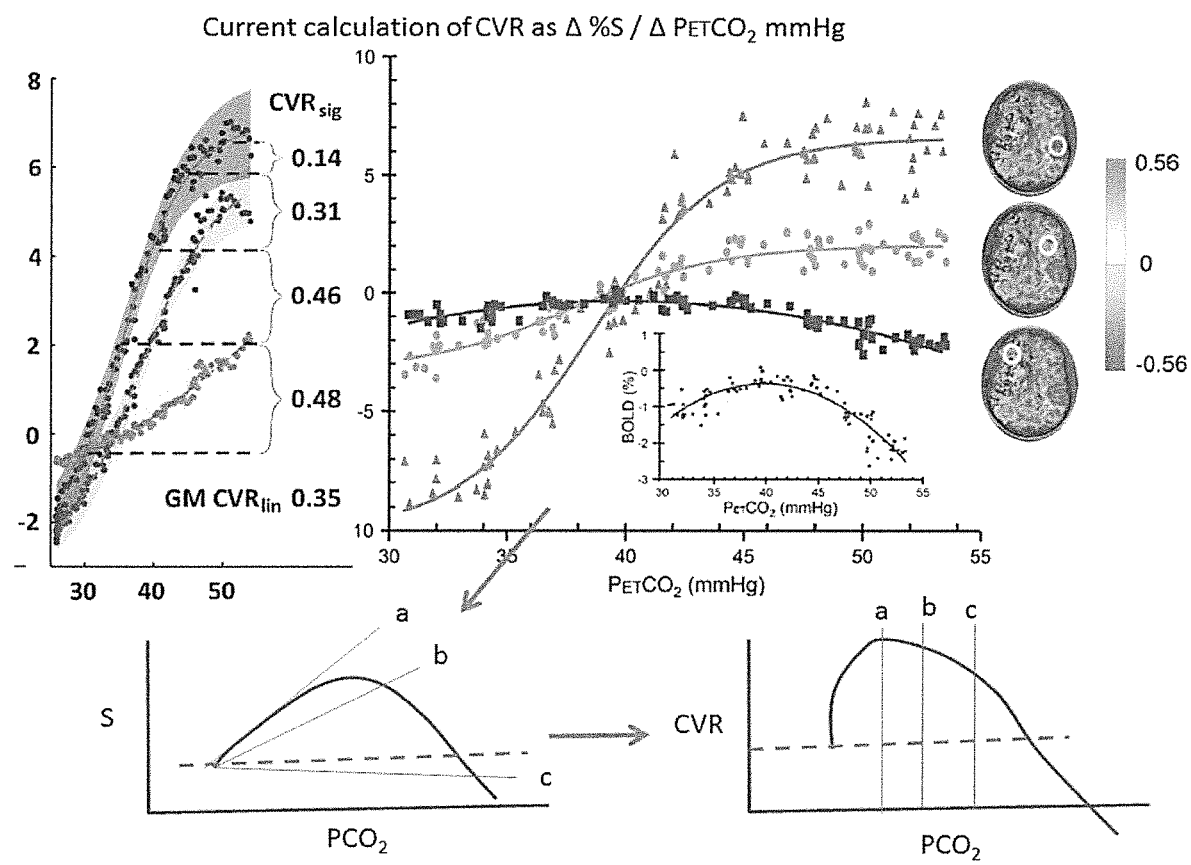
FIG. 4 is a set of graphs depicting response signals corresponding to a set of increments in $PCO_2$ from which CVR can be seen to be calculated as a change in BOLD signal as a function of increment changes in $P_{ET}CO_2$, and related CVR maps and conceptual graphs.

FIG. 4 includes a set of graphs from which CVR can be seen to be calculated as a function of $P_{ET}CO_2$, and related conceptual graphs. In the top left panel, the results of BOLD vs. $P_{ET}CO_2$ is illustrated in healthy gray matter and white matter with a Ramp sequence. The top right panel graph shows relationships between BOLD and $PCO_2$ in a pathological voxel in a scan in a patient with carotid stenosis. The bottom right panel show the analysis of CVR (slope) for a pathological voxel in the course of progressively greater $P_{ET}CO_2$. The bottom right panel shows the same data in which CVR is a function of $P_{ET}CO_2$. Even after the BOLD signal begins to decline with increasing $PaCO_2$, the CVR stays positive, reducing the sensitivity of the CVR measure.

Figure 5:
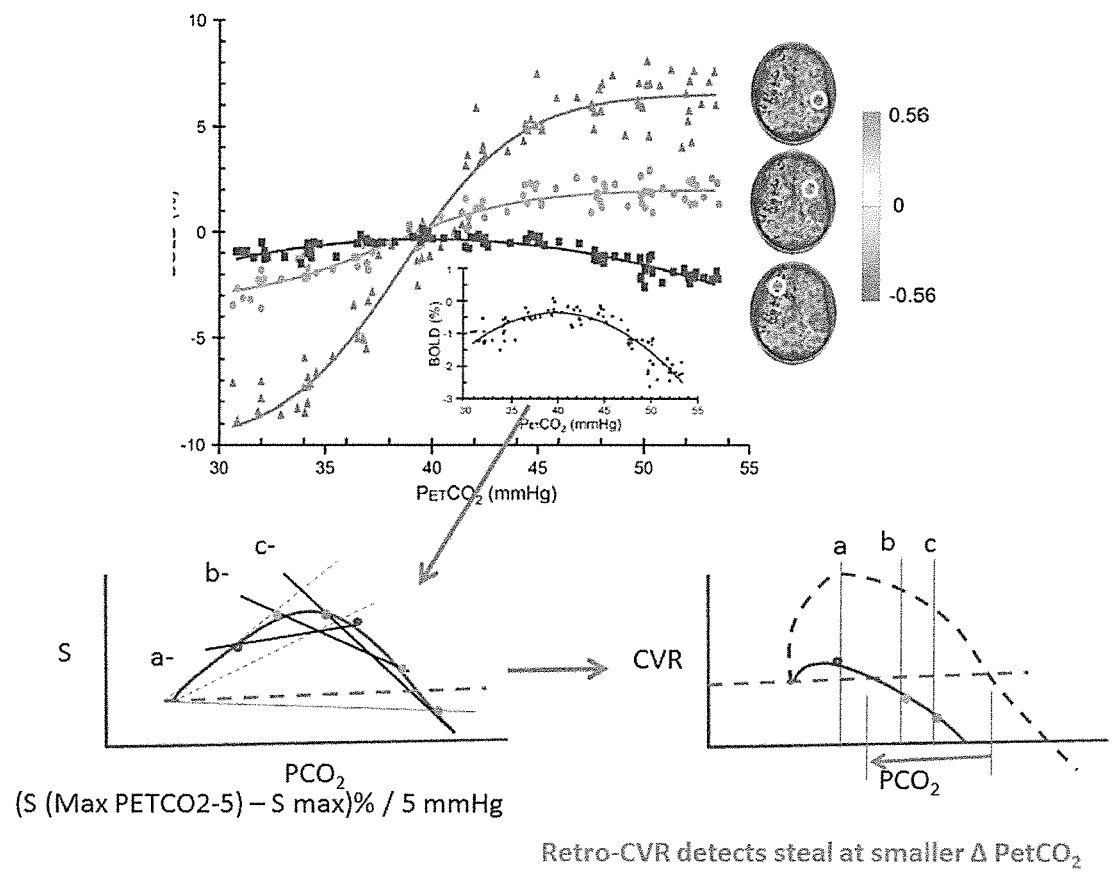
FIG. 5 is a set of graphs depicting response signals corresponding to a set of increments in $PCO_2$ from which CVR can be seen to be calculated as a change in BOLD signal as a function of increment changes in $P_{ET}CO_2$, and related CVR maps and conceptual graphs.

As seen in FIG. 5, in one embodiment, an analysis can be performed to increase the sensitivity of identifying a pathological vascular response: the "reduced CVR". The upper graph is taken from Sobczyk et al 2014. In the lower left we present a schematic representation of the BOLD signal over the full range of increments in $PCO_2$. The lower left schematic also shows CVRs (slopes) computed for specific portions of the vasoactive response in the ROI, the specific portions of the response corresponding to a sub-range of increments and/or decrements in the vasoactive stimulus within the full range of the vasoactive stimulus. The highest sub-range of the vasoactive stimulus (the upper 5 mm of Hg) can be seen to most sensitive to quantifying a reduction in cerebrovascular reactivity. CVRs calculated for these sub-ranges, from the signals corresponding to the top of the investigated range (Smax):(S(max)-S(Smax minus 5 mm))/($P_{ET}CO_2$(max)-$P_{ET}CO_2$ (Smax-minus 5 mm of Hg) as well as from less discriminatory sub-ranges, from which the reduced slope is less apparent. Bottom right is a resulting graph of CVR vs. $P_{ET}CO_2$ (max)). It can be seen that this markedly increases the sensitivity of identifying abnormal vasculature and reduces the extent of $P_{ET}CO_2$ that must be attained to identify the dysfunction.

Figure 6:
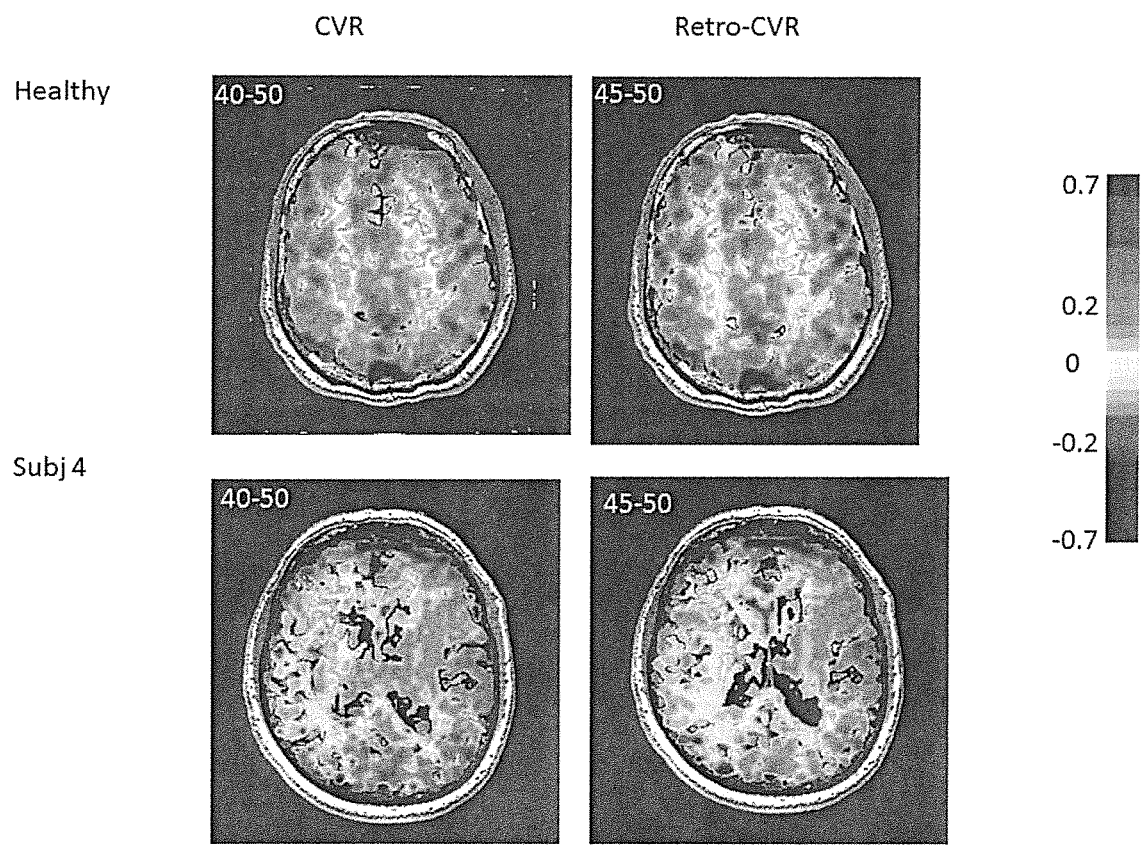
FIG. 6 is a series of CVR maps.
Figure 7:
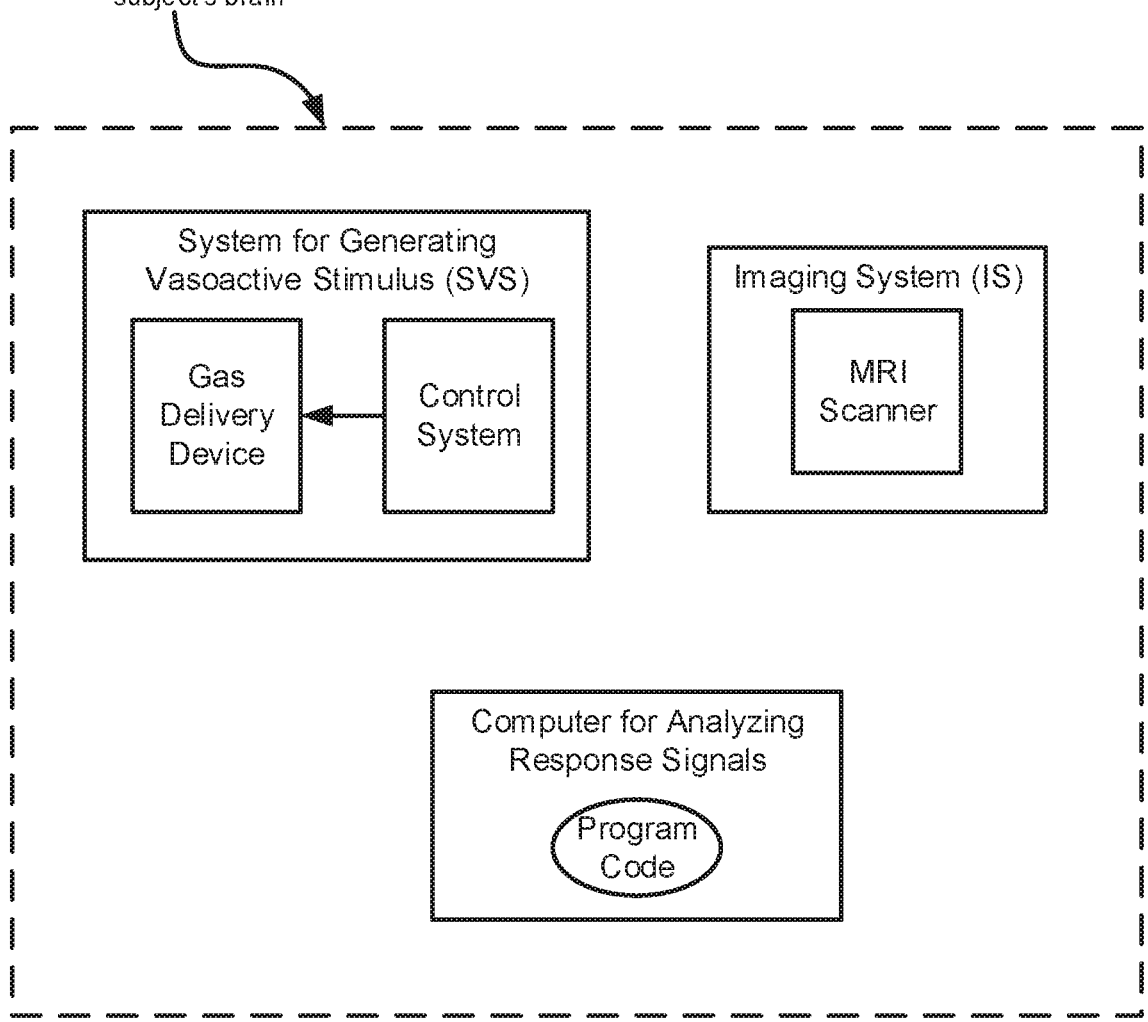
FIG. 7 is a block diagram of a system for detecting an abnormality in a subject's cerebrovascular response to a vasoactive stimulus in at least one region of interest (ROI) of the subject's brain.

FIG. 6 provides an example of an increased sensitivity of CVRs computed for upper sub-ranges in the vasoactive for quantifying a reduction in cerebrovascular reactivity in a healthy brain and diseased brain. On left are CVR maps computed for the entire range of the vasoactive stimulus. On right are the corresponding CVR maps computed a sub-range of the vasoactive stimulus. Both show greater sensitivity. The patient scan is more dramatic because there are more areas with abnormal vasculature and various degrees of abnormality, resulting in greater redistributions of blood flow.

Without being bound to a theory, the empirical observations of the inventors, are consistent with the following explanation. Because the vasodilatory response to increments in $PaCO_2$ is greatest at lower increments from baseline and begins to flatten out as $PaCO_2$ climbs, the lowest CVR will be at the high end of the $PaCO_2$ range. Since the measure of the cerebrovascular flow (e.g. BOLD signal) exhibits substantial measure-to-measure variability, larger ranges over which CVR is averaged result in principle, in better signal to noise ratios—but at the expense of averaging in CVR from parts of the stimulus profile that include higher CVR values; values that when included in the calculation, lead to the overestimation of the CVR.

In practice, the greater the range of $PaCO_2$ over which the CVR value is computed, the greater the number of measures and the less the influence of noise on the CVR. But, by including measures taken at lower $PaCO_2$s, the higher BOLD signals overestimate the CVR. Thus, by computing at least one CVR over a sub-range, the sub-range including approximately a 4 to 6 mm range (e.g. a 5 mmHg range) at approximately the top of the investigated range (the investigated range including, for example, approximately an 8 to 12 mm of Hg over baseline for the subject), enough data points are available with reduced weighting from the lower increments in stimulus and advantageously with a greater chance of revealing a pathology reflected in "steal", which might also be greatest at the highest range of $PaCO_2$s investigated.

The IS is optionally a "high resolution" imaging system. The term "high resolution" used with reference to imaging modality or device refers to an imaging modality enjoying a spatial resolution of 1 cubic centimeter or smaller. The term includes MRI imaging modalities (for example BOLD, T2*, ASL) and other imaging modalities well known as being useful to quantify surrogate measures of blood flow (CT, SPECT, PET). Proprietary and non-proprietary software for analyzing images in available to persons skilled in the art.

The present invention extends the analytic methods of CVR measurement to determine the region by region normal range of CVR and thereby enable quantification of abnormality by the assessment of CVR in terms of its deviation from a statistical mean. The inventors took an approach similar to that of Guimond et al. [Guimond A, 2000] and Seitz et al. [Seitz, 1990] who co-registered scans of healthy subjects into a standard space and determined the normal mean and variance of CVR, voxel-by-voxel. In one aspect, the present invention is directed to generating an atlas of images for non-pathological CVR response by co-registering $CO_2$ stimulated BOLD MRI CVR maps from a healthy cohort into a standard space, and calculating the mean and SD of the CVR for each voxel.

Example of MRI Protocol and CVR Map Generation

Magnetic resonance imaging may be performed with a 3.0-Tesla HDx scanner using an 8-channel phased-array receiver coil (Signa; GE Healthcare, Milwaukee, Wis.), and consisted of BOLD acquisitions with echo planar imaging (EPI) gradient echo (TR/TE=2000/30 ms, 3.75×3.75×5 mm voxels, field of view 24×24 cm, 39 slices, slice thickness 5 mm, matrix size 64×64, number of frames=254, flip angle (FA)=85°).

The acquired MRI and $PETCO_2$ data may be analyzed using AFNI software (National Institutes of Health, Bethesda, Md. $PETCO_2$ data may be time-shifted to the point of maximum correlation with the whole brain average BOLD signal. A linear, least-squares fit of the BOLD signal data series to the $PETCO_2$ data series (i.e., CVR) may then be performed on a voxel-by-voxel basis. For displaying CVR maps, voxels with a correlation coefficient between −0.25 and +30 0.25 may be eliminated before color-coding the remaining CVR values.

BOLD images may then be volume registered and slice-time corrected and co-registered to an axial 3-D T1-weighted Inversion-Recovery prepared Fast Spoiled Gradient-Echo (IR-FSPGR) volume (TI/TR/TE=450/8/3 ms, voxel size 0.86×0.86×1.0 mm, matrix size 256×256, field of view 22×22 cm, slice thickness=1 mm, FA=15°) that was acquired at the same time [Saad, 2009]. This method has been described in greater detail elsewhere [Fierstra, 2010].

Example of Analysis of CVR Maps

Constructing the Atlas (see also Guimond, A 2000, and Seitz, 1990).

Analytical processing software (SPMS; Wellcome Department of Imaging Neuroscience, University College, London, UK), may be used to co-register each of the individual brain volumes from the healthy cohort into MNI (Montreal Neurologic Institute) standard space using a 12-parameter affine transformation followed by nonlinear deformations to warp the brain volume of interest into an MNI template of identical weighting contrast. The T1-weighted FSPGR volume may be used to estimate the transformation normalization into standard space, as defined by a T 1 weighted MN1152 standard template.

A spatial smoothing of Full-Width Half-Maximum (FWHM) 5 mm may be applied to each voxel. Assumption for normality was tested using the Anderson-Darling test (the statistical test for normality provided in AFNI) with p values greater than 0.05 assumed to pass the test. As most voxels (60%) did pass this threshold, and these were diffusely distributed throughout the brain, the simplifying assumption was made that the CVR for each voxel was normally distributed. The mean ($\mu$) and associated standard deviation ($\sigma$) of CVR may be calculated (AFNI software [Cox, 1996]). Maps may then constructed for $\mu$ and coefficient of variation ($\sigma/\mu$) to characterize the atlas.

Example of CVR Z-map Generation

The generation of an individual's CVR z-map may consist of three steps. First, a spatial normalization of the individual's anatomical scan and CVR map [Ashburner, 1999] using a MNI152 SPM distributed template may be produced. Second, the CVR of each voxel (x) may be scored in terms of a z value (i.e., $z = (x-\mu)/\sigma$). Finally, a color may be assigned to each z score to indicate the direction and magnitude (in z values) of the differences from the mean of the corresponding atlas voxel. CVR and CVR z scores may be superimposed on the corresponding anatomical scans to allow comparison of the CVR and its z score. Note that CVR voxels that are positive but lower than the atlas mean for that voxel will have negative z scores. Greater specificity for identifying underlying vascular pathophysiology is optionally assumed to be connoted by greater absolute value of z scores and the confluence of similarly scored voxels in both CVR and CVR z-maps.

To clarify the colour coding used, it is pointed out that in the resulting z-map: (1) Patient CVR map voxels that are negative (blue) where the corresponding atlas CVR map voxels are positive, will have negative z-scores coded light blue to purple. (2) Patient CVR voxels that are positive but lower than the atlas CVR voxels will also have negative z-scores. (3) However, negative CVR voxels that are greater (towards the positive direction) than the corresponding atlas CVR voxel will nevertheless have a positive z-score. Greater specificity is connoted by greater z scores (for z-maps) and the confluence of similarly scored voxels (both CVR and z-maps).

All references identified herein are hereby incorporated by reference.

The invention claimed is:

1. A system for detecting an abnormality in a subject's cerebrovascular response to a vasoactive stimulus in at least one region of interest (ROI) of the subject's brain, comprising:

(A) a system for generating the vasoactive stimulus (SVS), the vasoactive stimulus comprising at least one of a series of targeted increments in the subject's end tidal concentration of carbon dioxide ($PetCO_2$) and a series of targeted decrements in the subject's $PetCO_2$, the SVS including:
(a) a gas delivery device; and
(b) a control system for controlling the gas delivery device, wherein the control system is operable to deliver controlled amounts of carbon dioxide effective to attain said at least one of a series of targeted increments or decrements in the subject's $PetCO_2$, for a series of respective intervals;

(B) an imaging system (IS) comprising an MRI scanner for generating response signals corresponding to the subject's vasoactive response to the vasoactive stimulus, the response signals constituting a surrogate measure of blood flow in the at least one ROI;

(C) a computer for analyzing the response signals, the computer including program code for computing at least one value representing a quantitative measure of the subject's cerebrovascular reactivity (CVR) for the ROI, wherein the at least one value is obtained for a specific portion of the subject's vasoactive response in the ROI, the specific portion of the subject's vasoactive response corresponding to a sub-series of the at least one of a series of targeted increments in the subject's $PetCO_2$ and a series of targeted decrements in the subject's $PetCO_2$, the sub-series characterized in that the specific portion of the subject's vasoactive response is the portion sensitive to quantifying a reduction in cerebrovascular reactivity.

2. A system as claimed in claim 1, further configured for computing, on a ROI by ROI basis (for at least one ROI), at least one score (per ROI) adapted for interpreting the at least one value.

3. A system as claimed in claim 2, wherein the system is further configured to adapt the score to visually depict the value.

4. A system as claimed in claim 2, wherein the system is further configured to compute the score to grade the amplitude of the subject's cerebrovascular reactivity (CVR).

5. A system as claimed in claim 2, wherein the score quantifies the extent to which the at least one value deviates from a range of that value computed for the corresponding ROI in a control cohort, the value computed for the control cohort per ROI for the specific portion of the response corresponding to the same sub-series of the at least one of a series of targeted increments in the subject's $PetCO_2$ and a series of targeted decrements in the subject's $PetCO_2$, wherein the score reflects statistical confidence that the at least one value represents a pathophysiological reduction in cerebrovascular reactivity (CVR).

6. A system as claimed in claim 2, wherein the computer includes program code for computing at least one of the value and the score on a voxel by voxel basis for a series of voxels within the larger ROI, each ROI being a voxel within a larger ROI.

7. A system as claimed in claim 6, wherein the computer includes program code for color coding the scores for the series of voxels and for representing the series of voxels on a cerebrovascular reactivity (CVR) map of the ROI.

8. A system as claimed in claim 1, wherein the system is further configured to visually depict, on an image of the ROI, at least one of value per ROI and a score computed for interpreting the at least one value.

9. A system as claimed in claim 1, wherein the system is further configured to compute, on a voxel by voxel basis, the at least one of value and a score computed for interpreting the at least one value.

10. A system as claimed in claim 1, wherein the at least one of value and a score computed for interpreting the at least one value is adapted to visually depict the amplitude of the subject's CVR on an anatomical image of a slice of the brain composed of a set of voxels constituting the at least one ROI.

11. A system as claimed in claim 1, wherein the sub-series of the at least one of a series of targeted increments in the subject's $PetCO_2$ and a series of targeted decrements in the subject's $PetCO_2$ is characterized in that it is more sensitive to quantifying a reduction in cerebrovascular reactivity than a quantitative measure of CVR computed using an alternative set of response signals, the alternative set of response signals corresponding to a full range of the at least one of a series of targeted increments in the subject's $PetCO_2$ and a series of targeted decrements in the subject's $PetCO_2$.

12. A system as claimed in claim 1, wherein the computer includes program code for identifying a sub-series of the at least one of a series of targeted increments in the subject's $PetCO_2$ and a series of targeted decrements in the subject's $PetCO_2$ that is sensitive to quantifying a reduction in cerebrovascular activity.

13. A system as claimed in claim 1, wherein the sub-series of the at least one of a series of targeted increments in the subject's $PetCO_2$ and a series of targeted decrements in the subject's $PetCO_2$ for which the at least one value is computed includes a portion of the at least one of a series of targeted increments in the subject's $PetCO_2$ and a series of targeted decrements in the subject's $PetCO_2$ for which the signal to noise ratio is adapted to discriminate a negative CVR.

14. A system as claimed in claim 1, wherein the sub-series of the at least one of a series of targeted increments in the subject's $PetCO_2$ and a series of targeted decrements in the subject's $PetCO_2$ corresponds to the highest 4 to 6 mm of Hg in the subject's $PetCO_2$, an upper range of the stimulus selected such that the stimulated blood flow demand, for the ROI, exceeds the blood flow supply to an extent that results in a relative distribution of blood flow in favor of healthy vessels at the expense of vessels that have a reduced CVR.

15. A system as claimed in claim 14, wherein the upper range of stimulus is at least 8 to 12 mm of Hg above the subject's baseline carbon dioxide partial pressure ($PaCO_2$).

16. A system as claimed in claim 1, wherein the computer includes program code for computing at least one CVR for the specific portion of the response corresponding to the sub-series of the at least one of a series of targeted increments in the subject's $PetCO_2$ and a series of targeted decrements in the subject's $PetCO_2$, program code for determining whether or not the at least one CVR that is computed for this specific portion of the subject's vasoactive response represents a reduction in CVR, and program code for identifying a stimulus range or time range of the at least one portion of the vasoactive response for which the signal to noise ratio discriminates a reduced CVR within a relatively broader range of the vasoactive response, wherein inclusion in the analysis of a relatively broader range of the vasoactive response would result in a greater CVR value.

17. A system as claimed in claim 16, wherein the computer includes program code for identifying at least one portion of response that satisfies at least one of the following conditions:
  i) the stimulus range is sufficiently large to identify a reduced CVR and compute a slope of a tangent of a response curve;
  ii) the upper range of the stimulus is one in which stimulated blood flow demand exceeds the blood flow supply and results in a relative distribution of blood flow in favor of healthy vessels, at the expense of vessels that have a reduced CVR.

18. A system as claimed in claim 1, wherein a set of MR imaging protocols is used to generate a set of vasoactive response signals corresponding to each of the at least one of a series of targeted increments in the subject's end tidal concentration of carbon dioxide ($PetCO_2$) and a series of targeted decrements in the subject's $PetCO_2$.

19. A system as claimed in claim 18, wherein the vasoactive response signals represent a change in a blood oxygen level dependent (BOLD) response to a set of targeted incremental increases in a subject's $PetCO_2$, the vascular response values representing a change in BOLD MRI signal ($\Delta S$), in response to an increase in the $PETCO_2$ ($CVR=\Delta S/\Delta S\ PETCO_2$).

20. A system as claimed in claim 18, wherein the respective increments and/or decrements in the at least one of a series of targeted increments in the subject's $PetCO_2$ and a series of targeted decrements in the subject's $PetCO_2$ are administered at a controlled constant rate, optionally, the constant rate being an increase that reveals at least one to two time constant in progress of the response, optionally two to three time constants in the progress of the response.

21. A system as claimed in claim 1, wherein the computer includes program code for: a) fitting a polynomial to the vasoactive response that corresponds to a full range of the vasoactive stimulus; b) computing a first derivative of the polynomial; and c) identifying negative slopes corresponding to a specific portion of the vasoactive response for which the signal to noise ratio discriminates a negative CVR within a relatively broader range of the vasoactive response for which the CVR is positive.

* * * * *